United States Patent [19]
Wells et al.

[11] Patent Number: 6,124,348
[45] Date of Patent: Sep. 26, 2000

[54] VITAMIN C SKIN FORMULATIONS

[75] Inventors: Lawrence M. Wells, 93 Hoaglands La., Old Brookville, N.Y. 11545; Frederick H. Burmeister, Little Silver, N.J.

[73] Assignee: Lawrence M. Wells, Old Brookville, N.Y.

[21] Appl. No.: 09/109,217

[22] Filed: Jun. 30, 1998

Related U.S. Application Data

[60] Provisional application No. 60/252,757, Jul. 1, 1997.
[51] Int. Cl.⁷ .................................................. A61K 31/375
[52] U.S. Cl. ............................ 514/474; 424/45; 424/401; 424/486; 424/488
[58] Field of Search ...................................... 424/486, 488, 424/45; 514/474

[56] References Cited

U.S. PATENT DOCUMENTS

| | | | |
|---|---|---|---|
| 4,938,969 | 7/1990 | Schinitsky et al. | 424/642 |
| 5,122,536 | 6/1992 | Perricone | 514/474 |
| 5,561,158 | 10/1996 | Yu et al. | 514/557 |
| 5,733,572 | 3/1998 | Unger et al. | 424/450 |

*Primary Examiner*—Richard L. Raymond
*Assistant Examiner*—Ben Schroeder
*Attorney, Agent, or Firm*—Dara L. Onofrio

[57] ABSTRACT

A skin formulation comprising ascorbic acid suspended as a dispersion in a non-aqueous vehicle. The non-aqueous vehicle comprises a volatile organic solvent and a gelling base. The formulation provides a unique delivery system of Vitamin C to the skin.

16 Claims, No Drawings ial application No. 60/052,757 filed Jul. 1, 1998 which is incorporated herein by reference.

VITAMIN C SKIN FORMULATIONS

This application claims the benefit of U.S. provisional application No. 60/052,757 filed Jul. 1, 1998 which is incorporated herein by reference.

FIELD OF THE INVENTION

The present invention relates to skin formulations including ascorbic acid (Vitamin C), a volatile organic solvent and a gelling base. The invention also relates to a method of delivering stable Vitamin C to the skin.

BACKGROUND OF THE INVENTION

Vitamin C, also known as L-ascorbate, being a water-soluble vitamin is unstable in an aqueous medium. Thus, water-based cosmetic formulations including Vitamin C as a component are typically not stable. Eliminating water from the formulation cures this problem.

Currently produced and stable non-aqueous Vitamin C products contain either waxes or combinations of waxes and oils to promote stability of the suspensions but leave an oily or waxy residue on the skin after use which is unappealing and unaesthetic. In general aqueous formulations containing modifications of Vitamin C have proven either very expensive or otherwise limiting to the commercialization of a Vitamin C containing consumer product.

Vitamin C has been shown to be beneficial to the skin when used in formulae such as "Citrix", which is an oil-wax suspension. This formulation has aesthetic problems in that it leaves a greasy coating on the skin. However, it does provide an occlusive coating on the skin which allows the vitamin to hydrate in the skin's own moisture, and which also enhances the delivery of the vitamin.

The invention formulation utilizes a liquid suspending medium and other beneficial agents to eliminate the aesthetic problems seen with all other oil-wax suspensions. It also has the following properties/characteristics: faster penetration into the skin due to the presence of low molecular weight lipids; presence of protective agents such as grape seed oil; improved hydrophobic barrier such as PMMA beads FHC (perfluoropolymethyl isopropyl ether—tradename: FOMBILIN-HC available from Ausimont SpA); non greasy feeling due to the volatile hydrocarbon base and a wax-free formulation. The invention provides a unique formulation having these characteristics and as also provides a stable form of Vitamin C for delivery to the skin.

In general, formulations containing ascorbic acid are known in the art. For example, U.S. Pat. No. 5,561,158 to Yu et al. discloses compositions containing 2-hydroxycarboxylic acids and related compounds including ascorbic acid, that are applied to the skin to alleviate or improve skin lines, botches, blemishes, nodules, wrinkles, etc. Yu et al. discloses further that the 2-hydroxycarboxylic acids and their related compounds are "dissolved" in a solution prepared from ethanol, water, propylene glycol, butylene glycol, acetone or other pharmaceutically acceptable vehicle.

Another example is U.S. Pat. No. 5,122,536 to Perricone which discloses a method for the therapeutic treatment of psoriasis in which ascorbic acid, or a precursor of derivative thereof, is topically applied to the affected skin areas. In the Perricone compositions the ascorbic acid is provided in the form of the acid per se or in the form of a precursor or derivative. Suitable carriers include water, alcohols, oils and the like chosen for their ability to "dissolve or disperse" the active ingredient.

Still another example of compositions which include ascorbic acid is described in U.S. Pat. No. 4,938,969 to Schinitsky et al. Schinitsky et al. discloses a composition for reducing wrinkles by applying a topical formulation containing ascorbic acid, tyrosine and a non-toxic zinc salt. These formulations are incorporated into a tissue compatible vehicle such as hydrophilic lotion, ointment, cream, or gel-based vehicles. Examples of such vehicles are commercially available as "Dermabase" and "Unibase" formulations.

As described in the representative art, formulations containing ascorbic acid for use in various skin applications are shown. However, in the compositions described in Yu et al. and Perricone patents the ascorbic acid component is "dissolved" in an aqueous vehicle and in the Schinitsky patent the ascorbic acid is combined with tyrosine and a non-toxic zinc salt.

Advantage of the present invention over the known art is in the delivery system of Vitamin C to the skin. As previously mentioned, it is known that Vitamin C is not stable in water or in water-based cosmetic formulations. Surprisingly, the non-aqueous vehicle of the invention suspends anhydrous, particulate Vitamin C so that it can be applied in the manner similar to water containing lotions. In addition, the present composition, preferably, does not contain waxes, oils or silicone materials thus when it is applied to the skin it evaporates from the skin without leaving a waxy or oily residue left behind.

Thus it is an object of the invention to provide a means of dispensing Vitamin C in a liquid vehicle that embodies the desirable properties of formulations in which Vitamin C is not stable. The formulation of the present invention provides a non-aqueous viscous liquid that suspends the insoluble Vitamin C. The formulation is applied to the skin in a manner similar to water containing lotions and evaporates from the skin following application and leaves no waxy residue. The formulation is preferably wax, oil and silicone free, but these components may be included as optional ingredients. A preferred formulation is comprised of ascorbic acid, a volatile organic solvent and a gelling base.

The advantages of this invention over the prior art is that the application of the ascorbic acid (Vitamin C) is provided in a non-waxy, viscous liquid with adequate suspending ability so as to provide vitamin stability with long term uniform dosage of the Vitamin C.

SUMMARY OF THE INVENTION

In the present invention, these purposes, as well as others which will be apparent, are achieved generally by providing skin formulations comprising Vitamin C (ascorbic acid), and a non-aqueous vehicle which includes a volatile organic solvent, preferably isodecane, and a gelling base. Additional ingredients such as antioxidants, UV absorbing compounds and other materials may be added to the formulations to enhance the properties of the composition.

The Vitamin C present in the formulations is in substantially pure form. The non-aqueous vehicle of the invention provides a unique homogeneous suspension of the Vitamin C which is in an anhydrous, particulate state. The components of the non-aqueous vehicle stabilize the Vitamin C and do not react or solubilize the vitamin.

Other objects, features and advantages of the present invention will be apparent when the detailed description of the preferred embodiments of the invention are considered, which should be construed in an illustrative and not limiting sense as follows:

DETAILED DESCRIPTION OF THE INVENTION

In accordance with the present invention skin formulations comprising ascorbic acid suspended as a dispersion in a non-aqueous vehicle. The non-aqueous vehicle comprises both an organic solvent and a gelling base.

As used throughout the specification the terms ascorbic acid and Vitamin C are used interchangeably and are meant to refer to the same material.

The ascorbic acid used in the invention formulations has the formula $C_6H_8O_6$ (MW 176.1) and is a crystal structure soluble in water having a melting point of approximately 191° C. Vitamin C (L-ascorbate) is the preferred material used in the formulations. However, other forms of ascorbic acid can also be used and are selected from the group consisting of ascorbic acid, analogues of ascorbic acid, isomers of ascorbic acid, sugar-type derivatives of ascorbic acid, their salts and mixtures thereof. The biologically active form, L-ascorbic acid, is preferably used in the formulations.

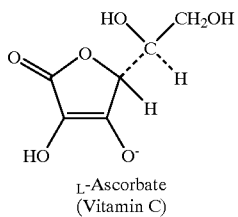

L-Ascorbate
(Vitamin C)

The ascorbic acid acts as an antioxidant and improves the development of collagen in the skin. The Vitamin C is present in the formulation as a dispersion in a non-aqueous liquid vehicle. The non-aqueous vehicle includes the organic solvent and gelling base components.

The terms "emulsions" and "dispersions" are often used interchangeably. In *Hackh's Chemical Dictionary*, 4th ed., 1969, a dispersed system (or dispersion) is defined as "an apparently homogeneous substance which consists of a microscopically heterogeneous mixture of two or more finely divided phases (solid, liquid or gaseous) e.g. liquid and liquid, solid and gas, etc." An emulsion is defined as "a suspension of a liquid in another liquid" and is considered a type of dispersion. As used in the specification herein in describing the invention coatings the general term "dispersion" is typically used. At ambient temperatures the invention compositions are generally solid/liquid dispersions.

The Vitamin C is present in the formulations in substantially pure form. The non-aqueous vehicle of the invention provides a unique homogeneous suspension of the Vitamin C which is in an anhydrous, particulate state. The components of the non-aqueous vehicle stabilize the Vitamin C and do not react with or solubilize the vitamin.

The gelling base used in the invention is a polymer solution comprising isododecane and polyoxyethylene 16—polyoxypropylene 30—glycol. A preferable gelling base used in the invention is GEL BASE commercially available from Brooks Distribution Division, South Plainfield, N.J. GEL BASE has a viscosity of at least 50,000 cps. The viscosity of the gelling base and final product formulation can vary depending upon what type of product is desired, i.e. a lotion, a cream etc. Although, GEL BASE is a preferred material, any gelling base capable of suspending the Vitamin C, in an anhydrous form, therein as a homogenous dispersion can be used in the invention.

The organic solvents used in the invention are volatile hydrocarbons which when the composition is applied to the skin surface the solvents evaporate. Isododecane is a preferred solvent material, however, other volatile hydrocarbon solvents having the same effect can also be used.

When the formulations are applied to the skin the volatile solvent evaporates leaving a polymeric film with solid particulate matter (Vitamin C) therein left on the skin surface. This film provides a unique delivery system of Vitamin C into the skin. Moisture from the skin penetrates the polymeric material enough to dissolve the water-soluble Vitamin C present in film. The solubilized Vitamin C is then "delivered" or absorbed by the skin surface. The benefits of Vitamin C are well known, this material is an anti-oxidant and helps produce collagen and elastin.

Moisturizing agents or lubricating agents such a isopropyl palmitate, isopropyl myristate and C12–15 alcohols benzoate can also be incorporated into the formulations. These materials help lubricate and soften the skin after the organic solvent has evaporated and also act as a barrier to water loss.

The formulation preferably comprises 0.1 to 15.0 weight % of ascorbic acid; 0.1 to 80.0 weight % of an organic solvent; and 0.1 to 35.0 weight % of a gelling base. The weight %'s of the components are wet weight percents.

Additional ingredients in the formulations include antioxidants, UV absorbing compounds and other materials described herein.

The antioxidants which may be used in the formulations are selected from the group consisting of butylated hydroxyanisole, butylated hydroxytoluene, tocopherol, tocopheryl acetate, ascorbyl palmitate, retinol, retinyl palmitate, hydroquinone and proanthocyanadines (from Grape seed oil).

The ultra-violet absorbing compounds which may be used in the formulations are selected from the group consisting of octyl methoxycimmate, p-aminobenzoic acid, p-aminobenzoic acid esters, benzophenone-3 and other FDA approved sunscreens.

Other materials which may be added to the formulations include an insoluble slip-inducing material. As the formulation evaporates to dryness a noticeable "tackiness" and a "grittiness" on the skin develops. The presence of the slip inducing agent counteracts this undesirable property. The slip-inducing material used in the formulations is selected from the group consisting of boron nitride, nylon beads, PMMA beads (polymethyl methacrylate).

The formulation further comprising a means of dispensing an insoluble fluoropolymer such as PMMA Beads FHC (perfluoropolymethyl isopropyl ether—tradename: FOMBILIN-HC available from Ausimont SpA). The PMMA beads are coated with fluoropolymer to provide lubrication.

Lipidic materials may also be included in the formulations and also improve lubrication during application on the skin (rub-in). The lipidic materials are selected from the group consisting of isopropyl myristate, isopropyl palmitate, isopropyl lanolate, myristyl myristate, mineral oil, petrolatum, C12–15 alcohols benzoate, vegetable oil triglycerides, castor oil and isostearyl isostearate.

The formulation is preferably free of waxes, oils and silicone materials but may optionally contain these materials if desired. Waxes such as beeswax, oils such as mineral oil, triglyceride oils (vegetable oils) and silicones such as methicone and dimethicone may be included in the formulations.

All components of the formulations are combined together under agitation and at room temperature. The mixture is then homogenized to create a homogeneous dispersion. Specifically, as in the Examples herein, the gelling base is diluted in isododecane at room temperature using low shear (propeller) mixing until homogeneous. The ascorbic acid is added to the gelling base and mixed with low shear mixing until a uniform dispersion results.

The following examples illustrate the invention. These examples are merely representative and are not inclusive of all the possible embodiments of the invention.

EXAMPLE I

A skin formulation in accordance with the invention was prepared by combining all of the ingredients listed below with proper agitation at room temperature. The mixture was then homogenized.

| INGREDIENT | AMOUNT (weight %) |
| --- | --- |
| ISODODECANE | 0.1 TO 80% |
| ASCORBIC ACID | 0.1 TO 15% |
| GELLING BASE | 0.1 TO 35% |

EXAMPLE II

A skin formulation in accordance with the invention was prepared by combining all of the ingredients listed below with proper agitation at room temperature. The mixture was then homogenized.

| INGREDIENT | AMOUNT (weight %) |
| --- | --- |
| ISODODECANE[1] | 58% |
| GRAPE SEED OIL[2] | 1% |
| GELLING BASE[3] | 25% |
| BORON NITRIDE[4] | 3% |
| ASCORBIC ACID[5] | 10% |
| NYLON[6] | 1% |
| PMMA BEADS FHC[7] | 2% |

Isododecane[1] - Permethyl 99 AD from Presperse, South Plainfield, New Jersey;
Grape Seed Oil[2] - Brooks Distribution Division, South Plainfield, New Jersey;
Gelling Base[3] - GEL BASE - Brooks Industries, South Plainfield, New Jersey;
Boron Nitride[4] - #46 - Carde, South Plainfield, New Jersey;
Ascorbic Acid[5] - 323 Mesh - Sigma chemicals, St Louis, Missouri;
Nylon[6] - 12 - Lipo Chemicals, Patterson, New Jersey;
PMMA Beads FHC[7] - (perfluoropolymethyl isopropyl ether - tradename: FOMBILIN-HC available from Ausimont SpA) - Carde, South Plainfield, New Jersey.

As seen from the examples the invention formulations provide a unique delivery system of Vitamin C to the skin. It is known that Vitamin C is not stable in water or in water-based cosmetic formulations. Currently produced stable non-aqueous Vitamin C containing products include waxes and/or oils which leave an "undesirable" oily or waxy residue on the skin after use. The present invention compositions provide a unique non-aqueous vehicle that suspends the insoluble Vitamin C so that it can be applied in the manner similar to water containing lotions in that it evaporates from the skin following application, however, there is no waxy or oily residue left behind.

The invention now being fully described, it will be apparent to one of ordinary skill in the art that many changes and modifications can be made thereto without departing from the spirit or scope of the invention as set forth herein.

What is claimed is:

1. A skin formulation comprising ascorbic acid suspended as a dispersion in a non-aqueous vehicle;
   wherein said non-aqueous vehicle comprises an organic solvent and a gelling base.
2. The formulation according to claim 1, comprising:
   0.1 to 15.0 weight % of said ascorbic acid;
   0.1 to 80.0 weight % of said organic solvent; and
   0.1 to 35.0 weight % of said gelling base.
3. The formulation according to claim 1, wherein said organic solvent is a volatile hydrocarbon.
4. The formulation according to claim 3, wherein said volatile hydrocarbon is isododecane.
5. The formulation according to claim 1, further comprising a moisturizing or lubricating agent selected from the group consisting of isopropyl palmitate, isopropyl myristate and C12–15 alcohols benzoate.
6. The formulation according to claim 1, further comprising antioxidants.
7. The formulation according to claim 6, wherein said antioxidants are selected from the group consisting of butylated hydroxyanisole, butylated hydroxytoluene, tocopherol, tocopheryl acetate, ascorbyl palmitate, retinol, retinyl palmitate, hydroquinone and proanthocyanadines (from Grape seed oil).
8. The formulation according to claim 1, further comprising ultra-violet absorbing compounds.
9. The formulation according to claim 8, wherein said ultra-violet absorbing compounds are selected from the group consisting of octyl methoxycimmate, p-aminobenzoic acid, p-aminobenzoic acid esters, benzophenone-3 and FDA approved sunscreens.
10. The formulation according to claim 1, further comprising an insoluble slip-inducing material.
11. The formulation according to claim 10, wherein said slip-inducing material is selected from the group consisting of boron nitride, nylon beads, PMMA beads (polymethyl methacrylate).
12. The formulation according to claim 11, further comprising a means of dispensing an insoluble fluoropolymer.
13. The formulation according to claim 9, wherein said insoluble fluoropolymer is perfluoropolymethyl isopropyl ether.
14. The formulation according to claim 1, further comprising lipidic materials.
15. The formulation according to claim 14, wherein said lipidic materials are selected from the group consisting of isopropyl myristate, isopropyl palmitate, isopropyl lanolate, myristyl myristate, mineral oil, petrolatum, C12–15 alcohols benzoate, vegetable oil triglycerides, castor oil and isostearyl isostearate.
16. A method of delivering Vitamin C to the skin comprising:
    providing a skin formulation comprising ascorbic acid (Vitamin C) suspended as a dispersion in a non-aqueous vehicle;
    wherein said non-aqueous vehicle comprises an organic solvent and a gelling base;
    applying said skin formulation to the skin;
    wherein said organic solvent evaporates leaving a polymeric film with solid particulate matter (Vitamin C) therein on the skin;
    such that moisture from the skin penetrates said polymeric film enough to solubilize the water-soluble Vitamin C, whereby the solubilized Vitamin C is absorbed by the skin.

* * * * *